(12) United States Patent
Primack et al.

(10) Patent No.: US 7,952,692 B2
(45) Date of Patent: May 31, 2011

(54) METHOD AND APPARATUS FOR DETERMINATION OF ANALYTE CONCENTRATION

(75) Inventors: Harel Primack, Rishon Le-Zion (IL); Aharon Weinstein, Rehovot (IL)

(73) Assignee: Orsense Ltd., Ness Ziona (IL)

( * ) Notice: Subject to any disclaimer, the term of this patent is extended or adjusted under 35 U.S.C. 154(b) by 141 days.

(21) Appl. No.: 11/637,194

(22) Filed: Dec. 12, 2006

(65) Prior Publication Data
US 2008/0137066 A1    Jun. 12, 2008

(51) Int. Cl.
*G01N 33/48* (2006.01)
*G01N 21/00* (2006.01)
*A61B 5/00* (2006.01)

(52) U.S. Cl. ............ 356/39; 356/40; 356/41; 356/432; 600/310; 600/322

(58) Field of Classification Search .................. None
See application file for complete search history.

(56) References Cited

U.S. PATENT DOCUMENTS

| | | | | |
|---|---|---|---|---|
| 3,998,550 A * | 12/1976 | Konishi et al. | ................ | 356/39 |
| 4,013,417 A * | 3/1977 | Raffaele | ................ | 422/67 |
| 5,111,817 A | 5/1992 | Clark et al. | | |
| 5,239,185 A * | 8/1993 | Ito et al. | ................ | 250/573 |
| 5,372,135 A | 12/1994 | Mendelson et al. | | |
| 5,377,674 A * | 1/1995 | Kuestner | ................ | 600/328 |
| 5,529,065 A * | 6/1996 | Tsuchiya | ................ | 600/310 |
| 5,575,284 A * | 11/1996 | Athan et al. | ................ | 600/323 |
| 5,676,142 A * | 10/1997 | Miwa et al. | ................ | 600/310 |
| 5,694,931 A * | 12/1997 | Tsuchiya | ................ | 600/310 |
| 5,830,133 A * | 11/1998 | Osten et al. | ................ | 600/322 |
| 5,833,602 A * | 11/1998 | Osemwota | ................ | 600/310 |
| 6,041,247 A * | 3/2000 | Weckstrom et al. | ................ | 600/323 |
| 6,084,661 A * | 7/2000 | Mendelson et al. | ................ | 356/41 |
| 6,195,574 B1 * | 2/2001 | Kumar et al. | ................ | 600/323 |
| 6,246,894 B1 * | 6/2001 | Steuer et al. | ................ | 600/322 |
| 6,266,546 B1 | 7/2001 | Steuer et al. | | |
| 6,373,568 B1 * | 4/2002 | Miller et al. | ................ | 356/326 |
| 6,400,972 B1 | 6/2002 | Fine | | |
| 6,473,632 B1 | 10/2002 | Myers | | |
| 6,526,298 B1 | 2/2003 | Khalil et al. | | |
| 6,587,704 B1 | 7/2003 | Fine et al. | | |
| 6,606,509 B2 * | 8/2003 | Schmitt | ................ | 600/310 |
| 6,694,159 B2 * | 2/2004 | Hall et al. | ................ | 600/310 |
| 6,711,424 B1 | 3/2004 | Fine et al. | | |
| 6,714,805 B2 * | 3/2004 | Jeon et al. | ................ | 600/323 |
| 6,819,950 B2 * | 11/2004 | Mills | ................ | 600/322 |
| 6,907,279 B2 * | 6/2005 | Sato et al. | ................ | 600/322 |
| 6,939,310 B2 | 9/2005 | Matzinger et al. | | |
| 6,947,131 B2 * | 9/2005 | O'Mahony et al. | ................ | 356/218 |
| 7,029,628 B2 * | 4/2006 | Tam et al. | ................ | 422/68.1 |
| 7,248,909 B2 * | 7/2007 | Lee et al. | ................ | 600/322 |
| 7,526,328 B2 * | 4/2009 | Diab et al. | ................ | 600/310 |
| 7,809,416 B2 * | 10/2010 | Ota et al. | ................ | 600/316 |
| 2002/0173706 A1 * | 11/2002 | Takatani | ................ | 600/323 |

* cited by examiner

*Primary Examiner* — Tarifur Chowdhury
*Assistant Examiner* — Gordon J Stock, Jr.
(74) *Attorney, Agent, or Firm* — Browdy and Neimark, PLLC

(57) ABSTRACT

A method and system are presented for use in determination of the concentration of an analyte in a subject's medium. The medium is irradiated with at least two radiation components to produce detectable radiation responses of the medium thereto. These at least two radiation components are selected to have different mean wavelengths and such that the spectral bandwidth of at least one of said at least two radiation components is characterized by relatively high variability of the extinction coefficient of the analyte of interest across said spectral bandwidth. This enables analysis of data indicative of detected radiation responses of the medium to said at least two radiation components and determination of the concentration of said analyte.

49 Claims, 4 Drawing Sheets

METHOD AND APPARATUS FOR DETERMINATION OF ANALYTE CONCENTRATION

FIELD OF THE INVENTION

The present invention is in the field of analyte measurements, and relates to a method and apparatus for the determination of analytes concentration.

BACKGROUND OF THE INVENTION

In recent years, several techniques have been proposed for non-invasive determination of blood and tissue analytes, such as hemoglobin, glucose, bilirubin, cholesterol and others. Among the methods frequently used are methods that utilize light-matter interaction, especially of Red and Near-Infrared (RNIR) radiation through blood perfusion fleshy medium. Usually, the radiation consists of a plurality of wavelengths. Analyses of optical properties (absorption, scattering, transmission and/or reflection of different wavelengths) of blood, tissue or blood perfused fleshy medium assists in determination of the desired analyte concentration. For example, U.S. Pat. Nos. 5,111,817, 5,372,135, 6,266,546, and 6,473,632 disclose some of these techniques.

SUMMARY OF THE INVENTION

There is a need in the art to facilitate the determination of analyte concentration, especially but not limited to non-invasive determination, by providing a novel method and apparatus enabling to increase the accuracy of measurements.

The main idea of the present invention is based on the understanding that optical measurements of analyte concentration can be facilitated by selecting optimal parameters of the radiation sources to be used, and especially their spectral characteristics.

The invention utilizes radiation sources that have a continuous spectrum of radiation emission (spectral distribution), whereas this spectrum is characterized by two main parameters: the mean wavelength of radiation emission and the spectral width (e.g., half width at half height, standard deviation of the spectral distribution, etc.). Light Emitting Diode (LED) based sources are characterized by a relatively wide spectral width (typically about 20 nm-50 nm), while lasers have relatively narrow spectral width (typically less than 1 nm). The inventors have found that appropriate selection of the mean wavelengths and spectral widths for light sources to participate in a measurement enables optimal radiation source selection to thereby simplify the measurement, improve the accuracy of the analyte concentration determination and reduce the costs of the measurement device. The use of the principles of the invention is especially important in cases where the analyte does not exhibit sharp peaks of extinction within the measurement spectral range. The present invention provides a set of such spectral selection criteria that apply to LED and other broadband sources. For some kinds of measurements, LEDs have substantial advantage over lasers and other sources.

It should be understood that the term "extinction" is used here to signify the overall attenuation of light over the medium traversed due to absorption and/or scattering and/or possibly other optical, physical and light-matter interaction phenomena. In many cases, the extinction coefficient is not very different (in shape, magnitude or numerical values) from the absorption coefficient. Hence, the terms "extinction" and "absorption" are used somewhat interchangeably in this disclosure, with the most appropriate term being used according to the context.

There is thus provided according to one broad aspect of the invention, a method for use in measurements of the concentration of an analyte in a subject's medium, said method comprising: irradiating the medium with at least two radiation components during a certain measurement time to produce detectable radiation responses of the medium thereto, said at least two radiation components being selected to have different mean wavelengths and such that the spectral bandwidth of at least one of said at least two radiation components is characterized by relatively high variability of the extinction coefficient of the analyte of interest across said spectral bandwidth, thereby enabling analysis of data indicative of detected radiation responses of the medium to said at least two radiation components in order to determine the concentration of said analyte.

Preferably, said at least one radiation component (the spectral bandwidth of which includes a region of relatively high variability of the extinction coefficient of the analyte of interest) contains a plurality of wavelengths with radiation intensity that can be in a fixed relation to each other during the measurement time According to another broad aspect of the invention, there is provided a method for use in determination of a hematocrit concentration, the method comprising:
  providing at least two sources of electromagnetic radiation operable in different spectral regions;
  selecting an operating spectral bandwidth of at least one of said sources of radiation such that variability of an absorption coefficient of said hematocrit is substantial across the operating spectral bandwidth of said source;
  measuring the intensity of the radiation transmitted through and/or reflected from the medium radiation; and
  deriving from said transmitted and/or reflected radiation intensity the value of said hematocrit.

According to another broad aspect of the invention, there is provided a method for use in determination of the concentration of an analyte in a subject's medium utilizing illumination of the medium with at least two different radiation components during a certain measurement time and detecting radiation responses of the medium to said at least two radiation components, the method comprising: selecting said at least two radiation components to have different mean wavelengths such that the spectral bandwidth of at least one of said at least two radiation components is characterized by relatively high variability of an extinction coefficient of the analyte of interest across said spectral bandwidth and said at least one radiation component contains a plurality of wavelengths with radiation intensity being in a fixed relation to each other during the measurement time.

According to yet another broad aspect of the invention, there is provided a system for use in measuring the concentration of an analyte in a subject's medium, the system comprising a light source unit configured and operable to produce at least two radiation components having different mean wavelengths, with the spectral bandwidth of at least one of said at least two radiation components being characterized by relatively high variability of an extinction coefficient of the analyte of interest across said spectral bandwidth. According to yet further aspect of the invention, there is provided a system for use in determination of the concentration of an analyte in a subject's medium, the system comprising a measurement unit and a control unit connectable to the measurement unit, the measurement unit comprising a light source unit and a light detector unit, the light source unit being configured and operable to produce at least two radiation components having different mean wavelengths, with the spectral wavelength of at least one of said at least two radiation components being characterized by relatively high variability of an extinction coefficient of the analyte of interest across said spectral bandwidth and said at least one radiation component containing a plurality of wavelengths with radiation intensity being in a fixed relation to each other during the measurement time, the detector unit comprising one or more light detectors adapted for collecting the radiation components after being transmitted through and/or reflected from the illuminated medium and generating data indicative of the detected light components, the control unit being configured for analyzing said data to determine a relation between the detected light components and analyze said relation to derive therefrom the analyte concentration.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EXEMPLARY EMBODIMENTS

The method and apparatus according to the present invention may be understood with reference to the drawings and the accompanying description, wherein like numerals of reference designate like elements throughout the text of the disclosure.

Figure 1:
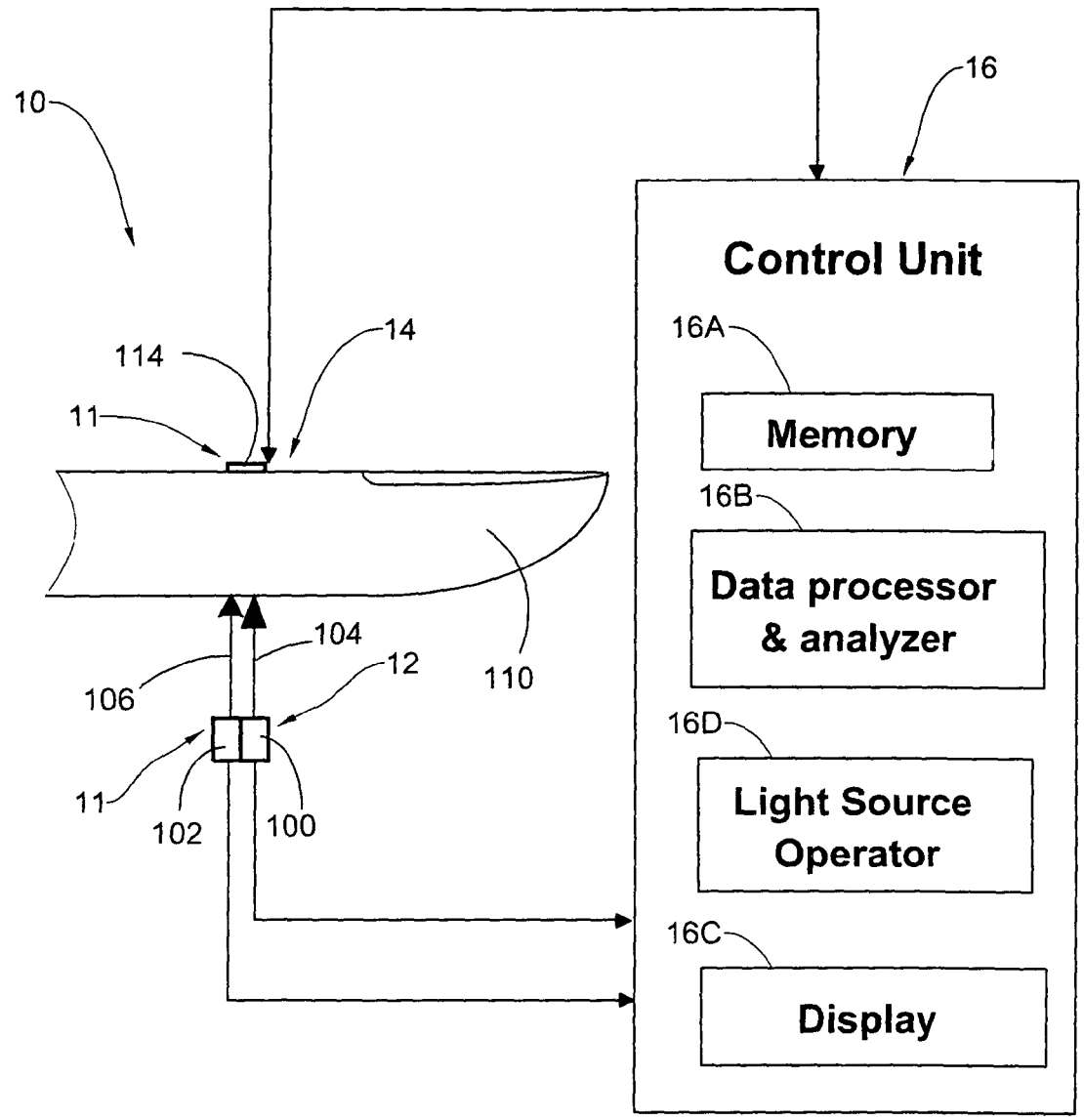
FIG. 1 is a schematic illustration of a set-up for analyte concentration determination, constructed according to the present method.

Reference is made to FIG. 1 showing schematically an optical apparatus, generally at 10, constructed and operated according to the present invention for use in the analyte concentration determination. Apparatus 10 includes an optical measurement unit 11 configured to be applied to a subject under measurements, and being connectable (via wires or wireless signal transmission) to a control unit 16. Measurement unit 11 includes an electromagnetic radiation (light) source unit 12 for illuminating the subject, and a light detection unit 14 for detecting a radiation response of the illuminated region of the subject.

In the present example, the measurement unit 11 is shown as being applied to a subject's finger 110 or a body part (constituting a subject), but it should be understood that the invention is not limited to this specific example. It should be understood that the invention is not limited to non-invasive measurements.

Also, in the present example the measurement unit 11 is configured for detecting a radiation response of the medium formed by transmission of the illuminating radiation through the subject's medium (finger). It should, however, be noted that the technique of the present invention is equally applicable to any radiation-matter interaction (generally "radiation response" of the subject's medium), including but not limited to transmission and/or reflection.

According to the present invention, the light source unit 12 includes at least two light sources—two such sources 100 and 102 are shown in the present example. The light sources 100 and 102 are selected such that at least one of these light sources has a spectral distribution characterized by that the variability of the extinction coefficient of an analyte of interest is substantial (of not less than about 5%) across the spectral width of this light source. This will be described more specifically further below with reference to FIGS. 2 and 3A-3B.

Preferably, the spectral characteristic of this at least one light source is in the form of a plurality of wavelengths, the intensity of which can be in a fixed relation to each other during the measurement time. A light source meeting this requirement is typically a LED.

The at least one other light source may also be such a LED or may be a narrow-band light source such as laser. In the present not-limiting example the use of two LEDs 100 and 102 is considered. Preferably, the LEDs operate in different spectral ranges.

The first and second LEDs 100 and 102 emit beams (radiation components) 104 and 106 of first and second electromagnetic radiation, respectively, which irradiate a part (measurement location) of subject's medium 110 over a certain time period (continuously or by timely separated sessions). Time variations of the radiation responses of the subject (transmission and/or reflection) are detected. Measured data indicative of the detected responses, being functions of time and wavelength, is received at the control unit 16, which operates to process this data to determine a relation between these two functions (e.g. a parametric slope of a time change of one function vs a time change of the other). As indicated above, preferably, at least one of the radiation sources (or each of them) emits a plurality of wavelengths, the intensity of which is in a fixed relation to each other during the measurement time. Typically, the spectral width of the LED is between 20 and 50 nanometers. Upon transmission of both beams 104 and 106 through the medium 110, such as a human body part (finger), a detector 114 (generally at least one detector) of detection unit 14 detects transmitted intensities of said first and second radiations.

The control unit 16 is typically a computer-embedded system including inter alia a memory utility 16A (e.g., for storing certain reference data, e.g., calibration data, calibration model, calculation model(s), etc.), a data processing and analyzing utility 16B preprogrammed to be responsive to measured data from the detection unit 14 for processing and analyzing this data and determining the analyte concentration, and a data output utility 16C (display). The control unit also includes a suitable operator utility 16D for controlling the operation of the light source unit. It should be noted, although not specifically shown, that the control unit includes an appropriate communication utility (not shown) to enable its connection (via wires or wireless) to the detection unit and possibly also to the light source unit, and may be configured for connection to another control/monitoring system via a communication network. To this end, the control system typically includes a data acquisition utility, such an A/D converter and appropriate electronics.

Thus, the present invention utilizes two or more radiation (light) components, where at least one of the light components has spectral distribution corresponding to as large as possible variability of the extinction of the analyte across this spectral distribution. Also, preferably, this at least one component includes a plurality of wavelengths with the wavelength intensity being a fixed relation to each other during the measurement time.

The use of a light source emitting a plurality of wavelengths with the wavelength intensity in a fixed relation to each other during the measurement time, for the purposes of the present invention is associated with the following.

Operating with narrow bandwidth light sources (monochromatic light), or broadband sources but with no fixed or predetermined relation between the wavelengths intensity, may not provide for selecting the optimal mean wavelength and spectral widths for incident light to be used in measurements. The problem is more essential in cases where the analyte does not exhibit sharp peaks of extinction within the measurement spectral range. When electromagnetic radiation impinges on a fleshy body part, such as a finger or an earlobe of a subject, that contains an analyte whose concentration is to be measured, such as hemoglobin and/or other radiation absorbing and/or scattering substances, the intensity of the detected response to said radiation (transmission and/or reflection) for a wide enough body part can be approximated for the purpose of explanation as follows:

$$I(\lambda,t) = I_0(\lambda) e^{-\alpha(\lambda)d(t)} = I_0(\lambda) e^{-H\beta(\lambda)d(t)}, \quad (1)$$

where I is the detected intensity of the radiation response, $I_0$ is the incident intensity (i.e., the intensity of light emitted by the radiation source and impinging on the body part), $\lambda$ is the incident radiation's wavelength, t is the irradiating time, $\alpha$ is an extinction coefficient of the radiation response, $\beta$ is an extinction coefficient per volume fraction of the analyte of interest of the radiation response, d is the effective width of the absorber, H is the volume fraction of the analyte of interest (e.g., Hematocrit in the case of blood), and $\alpha = H\beta$.

In order to extract physiological information from the detected intensity I, it is necessary to exclude from expression (1) the values of $I_0$ and d. U.S. Pat. Nos. 6,400,972, 6,587,704 and 6,711,424, all assigned to the assignee of the present application, teach methods of excluding these values by application of the so-called "Parametric Slope" (PS) method, where the PS is an example of a relation between the two radiation responses being functions of time and wavelength, and for the particular case is expressed as:

$$PS = \frac{\partial \ln I(\lambda_1, t)/\partial t}{\partial \ln I(\lambda_2, t)/\partial t} \quad (2)$$

where $\lambda_1$ and $\lambda_2$ are two selected incident radiation wavelengths.

Applying the parametric slope expressed in (2) to the above case expressed by (1), results in the following expression:

$$PS = \frac{H\beta(\lambda_1) \cdot d[d(t)]/dt}{H\beta(\lambda_2) \cdot d[d(t)]/dt} = \frac{\beta(\lambda_1)}{\beta(\lambda_2)}. \quad (3)$$

As shown, expression (3) is not explicitly dependent on the hematocrit H. Hence, to determine the hematocrit H with sufficiently high accuracy one may need an improved method, to be exemplified in the sequel, using a parametric slope as an example of a relation between the two light responses each being a function of time and wavelength.

Generally, the above expressions take into account a single wavelength for each light source, e.g., monochromatic light sources, such as lasers, where the effective optical coefficients (absorption and scattering) of the analyte of interest are substantially constant across the spectral bandwidth of the sources.

However, if the electromagnetic radiation (light) used in the measurements has a relatively broad spectral width with the wavelength intensity for multiple wavelengths being in a fixed relation to each other during the measurement time, then expression (2) is modified to include each and every spectral component of the radiation (light) source. Accordingly, using the superposition principle, one gets the expression for the parametric slope (PS) as follows:

$$PS = \frac{\partial \ln\left[\int d\lambda I^1(\lambda, t)\right]/\partial t}{\partial \ln\left[\int d\lambda I^2(\lambda, t)\right]/\partial t} \quad (4)$$

$$= \frac{\partial \ln\left[\int d\lambda I_0^1(\lambda) \exp(-H\beta(\lambda)d(t))\right]/\partial t}{\partial \ln[\int d\lambda I_0^2(\lambda) \exp(-H\beta(\lambda)d(t))]/\partial t},$$

where $I^1$ and $I^2$ are the detected intensities of electromagnetic radiation responses (intensities of transmitted and/or reflected light) resulting from illumination of the medium by light from the first light source $LED^1$ (100 in FIG. 1) and the second light source $LED^2$ (102 in FIG. 1), respectively. The quantities $I_0^1(\lambda)$ and $I_0^2(\lambda)$ are the spectral distributions of the incident intensity of the radiation emitted by the light sources $LED^1$ and $LED^2$, respectively.

Assuming a simple model in which both of the spectral distributions of the radiation sources, $I_0^1$ and $I_0^2$, are Gaussian, and the extinction coefficient per volume fraction of the analyte of interest $\beta$ changes linearly as a function of the wavelength within the LED spectral domain, the parametric slope has the following expression:

$$PS = \frac{\beta(\lambda_1) - H\gamma^2(\lambda_1)d\sigma_1^2}{\beta(\lambda_2) - H\gamma^2(\lambda_2)d\sigma_2^2} = f(H), \quad (5)$$

where $\lambda_1$ and $\lambda_2$ are the mean wavelengths of the radiation emitted by $LED^1$ and $LED^2$, respectively, $\sigma_1$ and $\sigma_2$ are their respective spectral widths, and $\gamma$ is determined as $\gamma \equiv \partial\beta/\partial\lambda$.

Since $\gamma\sigma \equiv \Delta\beta$ is the total change of the extinction coefficient per volume fraction of the analyte of interest $\beta$ across the spectral width of the light source, equation (5) can be rephrased as:

$$PS = \frac{\beta(\lambda_1) - Hd \cdot \Delta\beta_1^2}{\beta(\lambda_2) - Hd \cdot \Delta\beta_2^2}. \quad (6)$$

If the terms that contain the hematocrit H are relatively small, equation (6) can be approximated as:

$$PS = \frac{\beta(\lambda_1)}{\beta(\lambda_2)}\left[1 + Hd\left(\frac{\Delta\beta_2^2}{\beta(\lambda_2)} - \frac{\Delta\beta_1^2}{\beta(\lambda_1)}\right)\right]. \quad (7)$$

It should be noted that in equations (5-7), the parametric slope PS depends explicitly on the hematocrit H. Therefore, equations (5-7) prove that utilization of relatively broadband light sources with the wavelength intensity for multiple wavelengths in a fixed relation to each other during the measurement time (such as LEDs) is advantageous over the utilization of single-wavelength light sources (generally, narrow light sources) such as lasers, or broad band light sources with no fixed spectral distribution, for the determination of hematocrit. It should be understood that the above is equally valid for all other analytes that physically behave like indicated by equation (1).

It should be understood that equations (1-7) are presented as a non-limiting example. Specifically, a choice of Gaussian source distributions and linear variation of the extinction coefficients over the spectral distribution are exemplary and done for the brevity of exposition.

Specifically, as exhibited by equation (7), it is beneficial to have one of the sources devised such as to have as large as possible variability of the extinction across its spectral distribution, while the second one has as smaller variability as possible. This is due to the fact that the two terms within the innermost parentheses are both positive, and their difference multiplies H.

Thus, the present invention provides for a simple and precise method of determination the concentration of analytes due to the use of a light source (e.g. a LED) that emits a plurality of wavelengths, the intensity of which can be kept in a fixed relation to each other during the measurement time.

As indicated above, parametric slope is an example of a measurable relation between the medium radiation responses to different wavelengths over a certain time period. Other quantities, such as AC/DC ratios, which are sometimes used in such applications, may also benefit from the above mentioned method of using broadband light sources.

The accuracy of evaluating the hematocrit H from the parametric slope PS depends on the relative magnitude of the factors that appear in equation (5) as well as the accuracy of measuring the parametric slope PS, which is device and algorithm dependent. It may also depend on the quality of a calibration procedure, if the latter is required.

Figure 2:
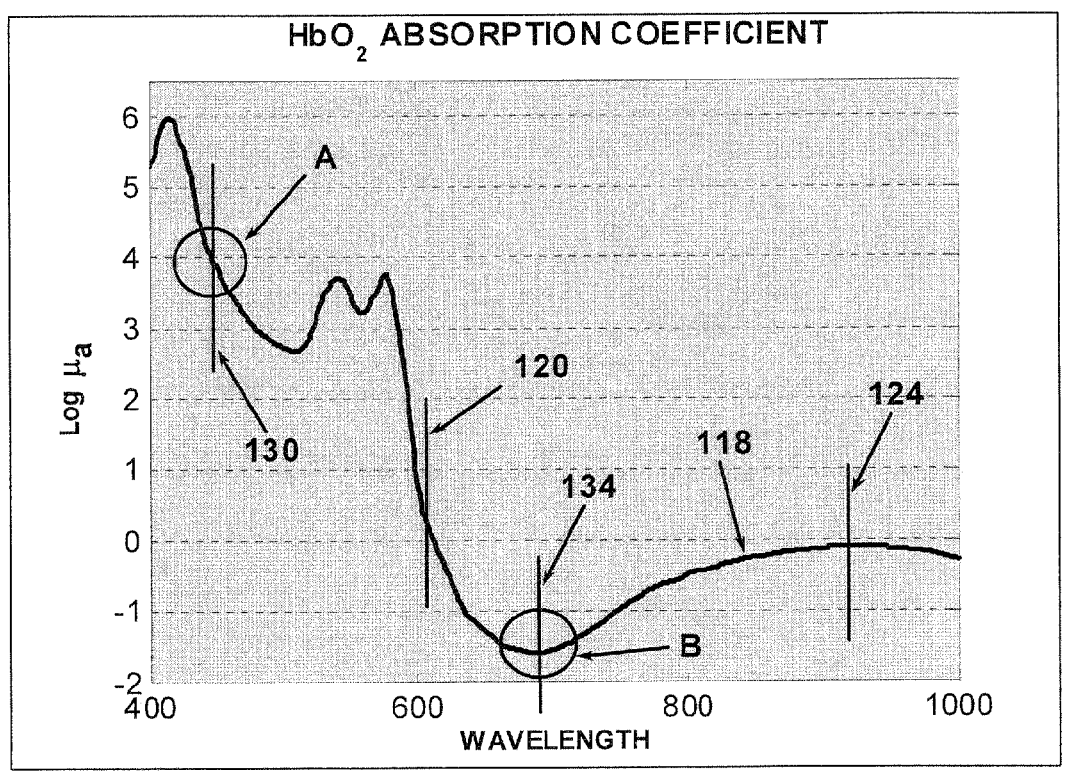
FIG. 2 is a schematic illustration of the absorption coefficient of hemoglobin as a function of the radiation wavelength.
Figure 3A:
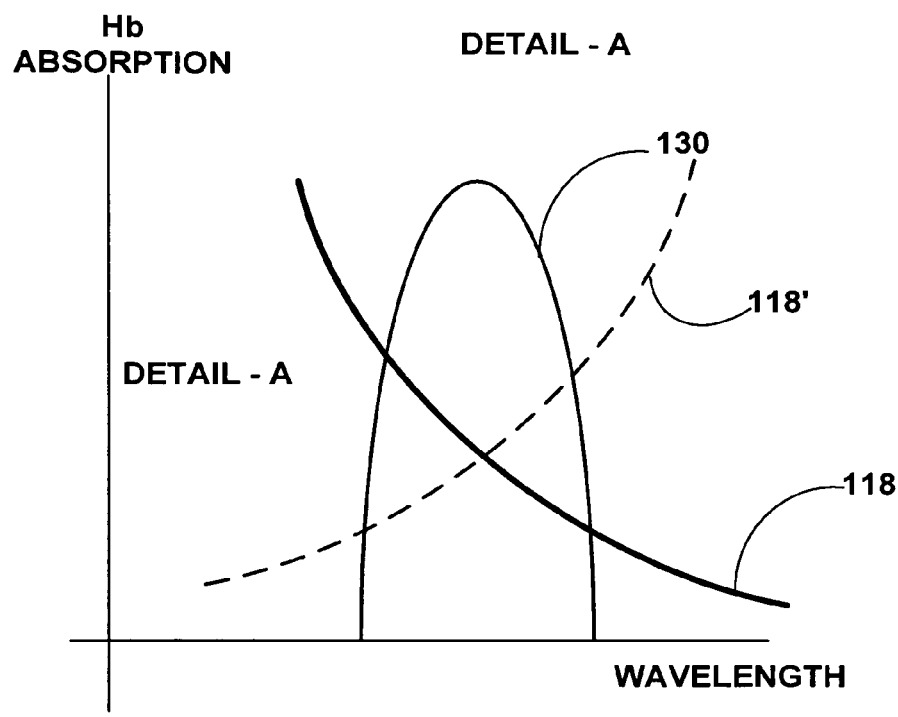
FIGS. 3A and 3B are schematic illustrations of the principle of the electromagnetic radiation sources mean wavelength selection according to the present method.
Figure 3B:
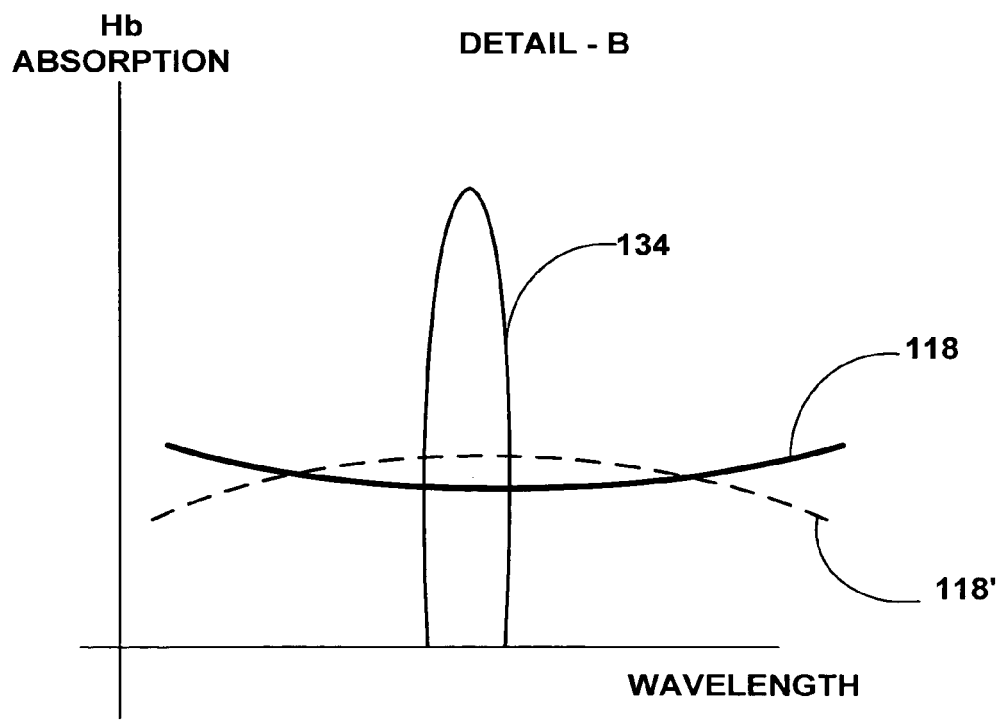

Reference is now made to FIGS. 2 and 3A-3B describing the principles of the invention for selecting optimal light sources (i.e. radiation components) to be used in the measurements. This consists of a proper selection of the mean wavelengths and spectral widths of the participating light sources (emitted radiation components). This selection is aimed at operating with at least one radiation component having a spectral width such that a region of relatively high variability of the extension coefficient of the analyte of interest occurs across this spectral width, and preferably operating with wavelengths of incident light produced by the two light sources corresponding to regions of high and low variability of the extinction coefficient of the analyte of interest.

FIG. 2 illustrates a graph 118 corresponding to the analyte (hemoglobin in the present example) absorption coefficient as a function of wavelength. The spectral domain of a multiple wavelength light source (LED$^1$ 100 in FIG. 1) is near a location 120, which is selected such that the variability of the absorption coefficient of hemoglobin across the spectral width of this light source is substantial. At least one other light source (LED$^2$ 102 in FIG. 1) is selected near location 124 where the variability of the absorption coefficient of hemoglobin across the spectral width of this source is small. Generally, this second light source may be a narrow band source, such as laser.

Turning back to FIG. 1, detector 114 detects the transmitted intensities of electromagnetic radiation components 104 and 106 and generates and communicates measured data to control unit 16. Data processing and analyzing utility 16B of the control unit operates to process the measured data by applying thereto the above equations (5-7) and determining the value of hematocrit. In addition to computing the parametric slope PS, explained above, it may be necessary beforehand to measure in-vivo this quantity for a plurality of subjects (patients) and generate a reference or calibration data base, to which the computed PS may be calibrated.

Turning back to FIG. 2, there is shown that in another embodiment of the invention, the mean wavelength location 130 of a spectral bandwidth of the first light source LED$^1$ (100 in FIG. 1) may be selected such that the variability of the absorption coefficient of hemoglobin is (locally) maximal across this spectral width. A spectral location 134 of a second source of radiation (102 in FIG. 1) is selected such that the variability of the absorption coefficient of hemoglobin across this spectral bandwidth is minimal. The spectral bandwidth of the second source 102 of radiation may be significantly narrower than that of the first source 100 of radiation. The second source of radiation 102 may even be a monochromatic source such as a laser.

In this connection, reference is made to FIGS. 3A and 3B showing more specifically regions A and B of graph 118 of FIG. 2. Per definition, the location with maximal variability across the spectral width would be a location where the first derivative of the hemoglobin absorption curve has maximal absolute value. The maximal value could be local, global or near maximal absolute value. The maximality needs to be determined according to the absorption curve as well as the available spectral range and/or the available radiation sources. The absolute value of the derivative is used, since equations (5-7) are indifferent to the sign of the change of the absorption coefficient across the spectral bandwidth of the radiation source. The location with maximal variability may be in an ascending section 118' or descending section 118 of the hemoglobin absorption coefficient curve. Considering the spectral bandwidth 134 of second source of radiation 102 (FIG. 3B), this region on the hemoglobin absorption curve is that where the value of the first derivative of the absorption curve is equal to zero or close to zero. It can be near a maximum, minimum, or an inflection point. It should be noted that the conditions of minimum and maximum can be relaxed in practice to being in the proximity of such minimum and maximum, respectively.

It should be appreciated that the number of such parameter pairs of mean wavelength and spectral bandwidths (defining a radiation source) on the extinction coefficient curve is practically unlimited. Although use of a single pair of light sources (where preferably at least one is a LED or generally a light source of a relatively broad spectral width with the wavelength intensity for multiple wavelengths in a fixed relation to each other during the measurement time) is sufficient for an analyte measurement, multiple pairs or other combinations of such light sources (e.g., LEDs) may be used to increase the accuracy of the measurement. For example, one can use a plurality of light sources, with one of them serving as the reference source. The accuracy of the measurement may be further increased by applying to the subject an occlusion or other types of artificial blood kinetics, such as disclosed in U.S. Pat. Nos. 6,400,972, 6,587,704 and 6,711,424, all assigned to the assignee of the present application, and as well as in U.S. Pat. Nos. 6,526,298 and 6,939,310.

Figure 4A:
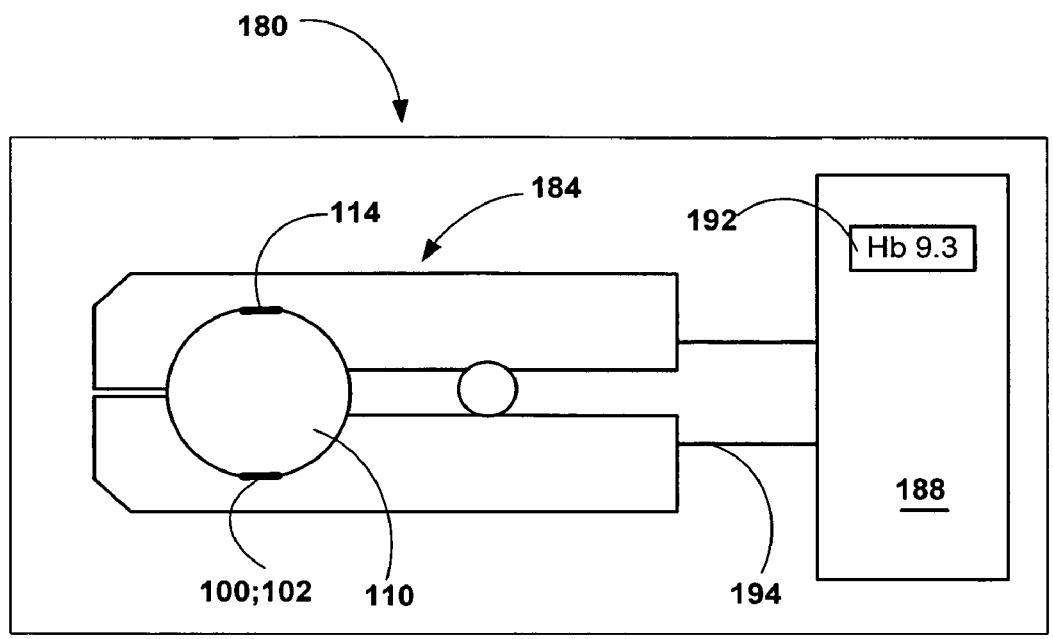
FIGS. 4A and 4B are schematic illustrations of exemplary embodiments of the apparatus for determination of an analyte concentration according to the present method.
Figure 4B:
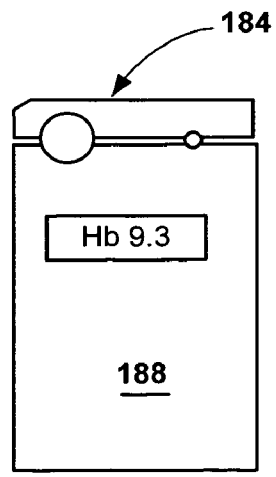

Reference is now made to FIGS. 4A and 4B showing specific but not limiting examples of the configuration of an apparatus 180 of the present invention for use in determination of an analyte concentration. As shown in FIG. 4A, apparatus 180 includes a clip-like holder (support) 184 for holding the subject's (patient's) fleshy medium (finger) 110 and a control unit or analyzer 188. Mounted on the holder 184 is a measurement unit formed by a light source unit (including two radiation sources 100 and 102) and a detection unit (including one or more light detector 114). The measurement unit is connectable to control unit 188 either by wire or wirelessly. The first source of radiation 100 is selected to have a mean wavelength and a spectral width such that the variability of the hemoglobin absorption coefficient is substantial across this spectral width. The second source of radiation 102 is selected such that the variability of the absorption coefficient of hemoglobin across the spectral width of this source is substantially different from that of first source 100, e.g., it is practically zero. Physically, the first and the second sources of radiation may be implemented as a multichip LED on the same substrate. Alternatively, LED, laser and other narrow-band and broadband sources may be combined on the same platform or substrate (e.g., matrix). Detector 114 detects the radiation response of the medium to radiation emitted by first 100 and second 102 radiation sources (detects transmission of the emitted radiation through subject fleshy medium in the present not-limiting example). The control unit or analyzer 188 communicates with the detector 114, receives measured data, analyzes the intensity of the radiation response (radiation transmitted through blood perfused fleshy medium), and derives a value of the desired blood analyte concentration. The control unit 188 may control operation of the light sources 100 and 102, display the results as illustrated in 192, as well as communicate with other devices and processes that may be required for analyte concentration determination. In the example of FIG. 4A, the apparatus 180 is made of two separate units: holder 184 carrying the measurement unit and controller or analyzer 188, which are connected by cables 194. As exemplified in FIG. 4B, the apparatus may alternatively be implemented as a single unit or housing incorporating the constructional elements of holder 184 (with radiation sources 100, 102 and detector 114) and those of analyzer unit 188.

Disclosed supra radiation sources bandwidth and mean wavelength selection are mutatis mutandis applicable to any apparatus configurations. One of the characteristics of at least one light source required for the purposes of the present invention is that the mean wavelength of the emitted spectrum corresponds to a wavelength region of substantial variability of the analyte's extinction and that this at least one light source emits a plurality of wavelengths, the intensity of which can be in a fixed relation to each other during the measurement time. A typical spectral width of a LED may be 20-50 nanometers.

The method disclosed above allows construction of a relatively simple and accurate apparatus for non-invasive determination of analytes. It is appreciated that although the general principles of the invention are more specifically exemplified above on hemoglobin, this technique is applicable to other analytes such as glucose, bilirubin, cholesterol and others. The method is especially suitable to analytes having at least two sections with different variability on the analyte extinction curve.

While the exemplary embodiment of the present method have been illustrated and described, it will be appreciated that various changes can be made therein without affecting the spirit and scope of the method. The scope of the method, therefore, is defined by reference to the following claims.

The invention claimed is:

1. A method for use in measurements of the concentration of an analyte in a medium having a certain extinction coefficient spectrum, said method comprising:

providing a selected light source unit capable of generating at least first and second radiation components, each having a selected mean wavelength and a selected spectral bandwidth such that the mean wavelength and spectral bandwidth of said first radiation component correspond to a first spectral region of the extinction coefficient spectrum of said analyte where variation of an extinction coefficient, $\Delta\beta_1$, per volume fraction of the analyte across the spectral bandwidth of the first radiation component is higher than in other spectral regions of the extinction coefficient spectrum, and the mean wavelength and second spectral bandwidth of said second radiation component correspond to a second spectral region of the extinction coefficient spectrum where variation of an extinction coefficient, $\Delta\beta_2$, per volume fraction of the analyte across the spectral bandwidth of the second radiation component is smaller than in other spectral regions of the extinction coefficient spectrum, and at least one of said at least two radiation components contains a plurality of wavelengths with radiation intensities that are in a fixed relation to each other during periods of said measurements;

irradiating the medium with said at least first and second radiation components during a certain measurement time to thereby produce detectable radiation responses of the medium thereto, analyzing data indicative of detected radiation responses of the medium to said at least first and second radiation components to determine the concentration of said analyte.

2. The method of claim 1, comprising applying at least two different sources of radiation to the medium to irradiate it by said at least two radiation components, respectively.

3. The method of claim 1, wherein said selecting of the mean wavelength of the spectral bandwidth for at least one of said at least two radiation components to be used in the measurements comprises analyzing data indicative of the extinction coefficient spectrum of the analyte of interest.

4. The method of claim 1, wherein the mean wavelength and the spectral bandwidth of at least one of said at least two radiation components are selected such that the variability of the extinction coefficient of said analyte across this spectral bandwidth is one of global and local maxima in absolute value.

5. The method of claim 1, wherein the mean wavelength of said at least two radiation components contains red-near infrared optical spectral regions.

6. The method of claim 1, wherein the mean wavelength of said at least two radiation components is within about 400 nm-2300 nm.

7. The method of claim 1, wherein the radiation responses comprise intensities of at least one of transmitted and reflected radiation through and from an irradiated part of the medium, respectively, for said at least two radiation components.

8. The method of claim 1, wherein said analyte is one of the following: hemoglobin, hematocrit, glucose, oxygen saturation, cholesterol, albumin and bilirubin.

9. The method of claim 1, wherein said analyte is a blood analyte.

10. The method of claim 1, wherein said analyte is a tissue analyte.

11. The method of claim 1, wherein said medium is a finger.

12. The method of claim 1, wherein said medium is a fleshy body part.

13. The method of claim 1, wherein at least one of said at least two radiation components is emitted by at least one Light Emitting Diode (LED).

14. The method of claim 1, wherein at least said first radiation component is emitted by a Light Emitting Diode (LED), and at least said second radiation component is emitted by a laser source.

15. The method of claim 1, wherein at least said first radiation component is emitted by a broadband light source configured for emitting the plurality of wavelengths with radiation intensities that can be in a fixed relation to each other during the measurement time.

16. The method of claim 1, comprising detecting said radiation responses as functions of time and wavelength, analyzing data indicative thereof for said at least two radiation components to determine a measurable relation between the detected radiation responses, and analyzing said relation to determine the analyte concentration.

17. The method of claim 13, wherein at least one of said at least two radiation components is emitted by at least one monochromatic source.

18. The method of claim 14, wherein said at least one LED has the spectral bandwidth of about 20-50 nm.

19. The method of claim 15, wherein at least said first radiation component is emitted by at least one Light Emitting Diode (LED).

20. The method of claim 19, wherein said at least one LED has the spectral bandwidth of about 20-50 nm.

21. The method of claim 16, wherein said measurable relation is determined as a parametric slope PS:

$$PS = \frac{\partial \ln I(\lambda_1, t)/\partial t}{\partial \ln I(\lambda_2, t)/\partial t},$$

where $\lambda_1$ and $\lambda_2$ are the mean wavelengths of said two radiation components.

22. The method of claim 16, wherein said analyzing of the relation between the detected radiation responses comprises comparing said relation to pre-determined calibration data, and extracting the value of said analyte concentration.

23. The method of claim 16, wherein said measurable relation is in the form of a quotient of time derivatives of the logarithms of said at least two radiation responses.

24. The method of claim 22, wherein said pre-determined calibration data is obtained by measuring and analyzing the radiation responses for a plurality of subjects together with their respective analyte concentrations and generating the calibration data.

25. The method of claim 23, wherein said analyzing of the relation between the detected radiation responses comprises applying to said relation a linear-regression algorithm and extracting a desired value of said analyte concentration.

26. The method of claim 23, wherein said analyzing of the relation between the detected radiation responses comprises comparing said quotient to pre-determined calibration data, and extracting the value of said analyte concentration.

27. The method of claim 26, wherein said pre-determined calibration data is obtained by measuring and analyzing the radiation responses for a plurality of subjects together with their respective analyte concentrations and generating the calibration data.

28. A method for use in determination of a hematocrit concentration, the method comprising:
providing at least two sources of electromagnetic radiation operable in different spectral regions of a hematocrit absorption coefficient spectrum;
selecting an operating spectral bandwidth of at least one of said sources of radiation such that said spectral bandwidth lies within a first spectral region of the absorption coefficient spectrum where variation of an absorption coefficient, $\Delta\beta_1$, per volume fraction of said hematocrit as a function of wavelength is higher than in other spectral regions of said absorption coefficient spectrum and such that said spectral bandwidth contains a plurality of wavelengths with radiation intensities that are in a fixed relation to each other during a measurement time;
irradiating a medium with said radiation from said at least two sources of electromagnetic radiation during a certain measurement time to thereby produce detectable radiation transmitted through and/or reflected from the medium at said different spectral regions,
measuring the intensity of the radiation transmitted through and/or reflected from the medium at said different spectral regions; and
deriving from said transmitted and/or reflected radiation intensity a measurable relation between the medium radiation responses to different wavelengths, and analyzing said relation to determine the hematocrit concentration.

29. A method for use in determination of the concentration of an analyte in a subject's medium having a certain extinction coefficient spectrum, the method utilizing illumination of the medium with at least two different radiation components during a certain measurement time and detecting radiation responses of the medium to said at least two radiation components, the method comprising: selecting said at least two radiation components such that a first radiation component has a first mean wavelength and a first spectral bandwidth and the second radiation component has a second mean wavelength and a second spectral bandwidth, where the spectral bandwidth of said first radiation component lies within a first spectral region of the extinction coefficient spectrum where variation of an extinction coefficient, $\Delta\beta_1$, per volume fraction of the analyte as a function of wavelength is higher than in other spectral regions within said extinction coefficient spectrum, and the spectral bandwidth of the second radiation component lies within a second spectral region where variation of an extinction coefficient, $\Delta\beta_2$, per volume fraction of the analyte as a function of wavelength is smaller than in other spectral regions within said extinction coefficient spectrum, and at least said first radiation component contains a plurality of wavelengths with radiation intensity being in a fixed relation to each other during the certain measurement time, the plurality of wavelengths including at least two wavelengths that are spaced apart from one another along the first spectral region, a relation between the detected radiation responses being indicative of the concentration of said analyte.

30. A system for use in measuring the concentration of an analyte in a subject's medium having a certain extinction coefficient spectrum for said analyte, the system comprising a light source unit configured and operable to produce at least first and second radiation components selected such that said first radiation component has a first mean wavelength and a first spectral bandwidth and said second radiation component has a second mean wavelength and a second spectral bandwidth, where the spectral bandwidth of said first radiation component lies within a first spectral region of said extinction coefficient spectrum where variation of an extinction coefficient, $\Delta\beta_1$, per volume fraction of the analyte across the spectral bandwidth of the first radiation component is higher than in other spectral regions within said extinction coefficient spectrum and said second spectral bandwidth lies within a second spectral region where variation of an extinction coefficient, $\Delta\beta_2$ per volume fraction of the analyte across the spectral bandwidth of the second radiation component, is smaller than in other spectral regions, and said first bandwidth contains a plurality of wavelengths with radiation intensities that are in a fixed relation to each other during a measurement time, a detector unit comprising one or more light detectors for collecting light from the medium and generating data indicative thereof, and a control unit connectable to the light source unit and to the detector unit, and being configured for processing and analyzing said data indicative of the detected light to determine a measurable relation between the detected radiation responses, and analyze said relation to derive therefrom the analyte concentration.

31. The system of claim 30, wherein the spectral bandwidth of at least said second radiation component is selected such that the variability of the extinction coefficient of said analyte across this spectral bandwidth is minimum in absolute value.

32. The system of claim 30, wherein the mean wavelength of said at least two radiation components is within red-near infrared optical spectral regions.

33. The system of claim 30, wherein the mean wavelength of said at least two radiation components is within about 400 nm-2300 nm.

34. The system of claim 30, wherein said one or more light detectors are adapted to collect light of said at least two radiation components transmitted through and/or reflected from the illuminated medium.

35. The system of claim 30, wherein the control unit is preprogrammed to determine said measurable relation as a parametric slope PS:

$$PS = \frac{\partial \ln I(\lambda_1, t)/\partial t}{\partial \ln I(\lambda_2, t)/\partial t},$$

where $\lambda_1$ and $\lambda_2$ are the mean wavelengths of said two radiation components.

36. The system of claim 30, wherein said control unit is preprogrammed to analyze the determined measurable relation between the detected radiation responses by applying to said determined measurable relation a linear-regression algorithm and extracting a desired value of said analyte concentration.

37. The system of claim 30, wherein the spectral bandwidth of at least said first radiation component is selected such that the variability of the extinction coefficient of said analyte across this spectral bandwidth is maximal in absolute value.

38. The system of claim 30, wherein the control unit is preprogrammed to determine said measurable relation as a quotient of time derivatives of logarithms of said at least two detected radiation responses.

39. The system of claim 30, wherein said control unit is preprogrammed to analyze the determined measurable relation between the detected radiation components by comparing said determined measurable relation to pre-determined calibration data and extracting the value of said analyte concentration.

40. The system of claim 30, wherein said light source unit comprises at least one light source producing at least one of said at least two radiation components having a relatively broad spectral bandwidth, and at least one other light source producing light of a relatively narrow spectral bandwidth.

41. The system of claim 37, wherein the spectral bandwidth of at least said second radiation component is selected such that the variability of the extinction, coefficient of said analyte across this spectral bandwidth is minimum in absolute value.

42. The system of claim 39, wherein said calibration data is indicative of detected radiation responses recorded for a plurality of subjects together with their respective analyte concentrations.

43. The system of claim 38, wherein said control unit is preprogrammed to analyze the determined measurable relation between the detected radiation responses by comparing said quotient to pre-determined calibration data, and extracting the value of said analyte concentration.

44. The system of claim 43, wherein said calibration data is indicative of detected radiation responses recorded for a plurality of subjects together with their respective analyte concentrations.

45. The system of claim 40, wherein said at least one light source is a Light Emitting Diode (LED), and said at least one other light source is a laser.

46. The system of claim 40, wherein said at least one light source and said at least one other light source are Light Emitting Diodes (LEDs).

47. The system of claim 45, wherein said LED has the spectral bandwidth of about 20-50 nm.

48. The system of claim 46, wherein said LEDs have the spectral bandwidth of about 20-50 nm.

49. A system for use in determination of the concentration of an analyte in a subject's medium having a certain extinction coefficient spectrum, the system comprising a measurement unit and a control unit connectable to the measurement unit, the measurement unit comprising a light source unit and a light detector unit, the light source unit being selected to be operable to produce at least two radiation components such that a first radiation component has a first mean wavelength and a first spectral bandwidth and a second radiation component has a second mean wavelength and a second spectral bandwidth, where the spectral bandwidth of said first radiation component lies within a first spectral region of said extinction coefficient spectrum where variation of an extinction coefficient, $\Delta\beta_1$ per volume fraction of the analyte across the spectral bandwidth of the first radiation component, is higher than in other spectral regions within said extinction coefficient spectrum and the spectral bandwidth of said second radiation component lies within a second spectral region of said extinction coefficient spectrum where variation of an extinction coefficient, $\Delta\beta_2$ per volume fraction of the analyte across the spectral bandwidth of the second radiation component, is smaller than in other spectral regions within said extinction coefficient spectrum and said at least one radiation component containing a plurality of wavelengths with radiation intensity being in a fixed relation to each other during a measurement time, the light detector unit comprising one or more light detectors adapted for collecting the radiation components after being transmitted through and/or reflected from the illuminated subject's medium and generating data indicative of the collected light components, the control unit being configured for analyzing said data to determine a measurable relation between the collected light components and analyze said relation to derive therefrom the analyte concentration.

* * * * *

UNITED STATES PATENT AND TRADEMARK OFFICE
CERTIFICATE OF CORRECTION

PATENT NO.       : 7,952,692 B2                                      Page 1 of 1
APPLICATION NO.  : 11/637194
DATED            : May 31, 2011
INVENTOR(S)      : Aharon Weinstein et al.

It is certified that error appears in the above-identified patent and that said Letters Patent is hereby corrected as shown below:

Title Page, Item (12), delete "Primack" and insert -- Weinstein --.

Title Page, Item (75) Inventors: should read as:
Aharon Weinstein, Rehovot (IL);
Harel Primack, Rishon Le-Zion (IL)

Signed and Sealed this
Twenty-second Day of November, 2011

David J. Kappos
*Director of the United States Patent and Trademark Office*